(12) United States Patent
Fehr

(10) Patent No.: US 9,284,514 B2
(45) Date of Patent: Mar. 15, 2016

(54) PENTA/HEXAMETHYL-3,4,5,8-TETRA-HYDRO-1(2H)-NAPHTHALENONE DERIVATIVES WITH AROMATIC NOTES

(75) Inventor: Charles Fehr, Versoix (CH)

(73) Assignee: Firmenich SA, Geneva (CH)

( * ) Notice: Subject to any disclaimer, the term of this patent is extended or adjusted under 35 U.S.C. 154(b) by 162 days.

(21) Appl. No.: 14/128,650

(22) PCT Filed: Jun. 18, 2012

(86) PCT No.: PCT/EP2012/061589
§ 371 (c)(1),
(2), (4) Date: Dec. 23, 2013

(87) PCT Pub. No.: WO2013/004476
PCT Pub. Date: Jan. 10, 2013

(65) Prior Publication Data
US 2014/0148376 A1   May 29, 2014

(30) Foreign Application Priority Data

Jul. 7, 2011 (EP) .................................. 11173019

(51) Int. Cl.
*C11B 9/00* (2006.01)
*C07C 49/637* (2006.01)

(52) U.S. Cl.
CPC .............. *C11B 9/0053* (2013.01); *C07C 49/637* (2013.01)

(58) Field of Classification Search
CPC .................... C11B 9/0053; C07C 49/637
See application file for complete search history.

(56) References Cited

U.S. PATENT DOCUMENTS

| 3,927,083 A | 12/1975 | Hall et al. |
| 4,320,772 A | 3/1982 | Yoshida |
| 2006/0211598 A1* | 9/2006 | Fehr ................................ 512/13 |

FOREIGN PATENT DOCUMENTS

| EP | 1689728 | 4/2007 |
| WO | WO 2005/054220 A1 | 6/2005 |

OTHER PUBLICATIONS

International Search Report and Written Opinion, application PCT/EP2012/061589, mailed Oct. 4, 2012.

* cited by examiner

*Primary Examiner* — Bijan Ahvazi
*Assistant Examiner* — Lanee Reuther
(74) *Attorney, Agent, or Firm* — Winston & Strawn LLP

(57) ABSTRACT

The present invention relates to compounds of Formula (I), wherein the dotted line represents a carbon-carbon single or double bond and R represents a hydrogen atom or a methyl group; which are useful perfuming ingredients to impart odor notes of the musky-earthy and woody, aromatic-fresh type.

(I)

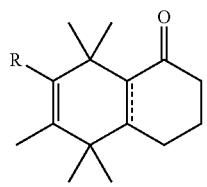

12 Claims, No Drawings

PENTA/HEXAMETHYL-3,4,5,8-TETRA-HYDRO-1(2H)-NAPHTHALENONE DERIVATIVES WITH AROMATIC NOTES

TECHNICAL FIELD

The present invention relates to the field of perfumery. More particularly, it concerns some penta/hexamethyl-3,4,5,8-tetrahydro-1(2H)-naphthalenone derivatives of formula (I), as defined below, which are useful perfuming ingredients. The present invention comprises also the invention's compounds as part of a perfuming composition or of a perfuming consumer product.

PRIOR ART

To the best of our knowledge, the invention's compounds of formula (I) are novel.

To the best of our knowledge, the closest analogues known in the perfumery and belonging to the same broad olfactive family are the ones described in EP 1689728, which have anyway a different structure and also a significantly different musk odor type. These prior art documents do not report or suggest any organoleptic properties of the compounds of formula (I), as discussed further below, and do not report or suggest any use of said compounds in the field of perfumery.

DESCRIPTION OF THE INVENTION

We have now surprisingly discovered that a compound of formula

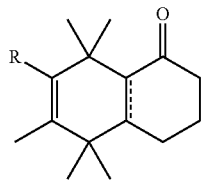

(I)

wherein the dotted line represents a carbon-carbon single or double bond and R represents a hydrogen atom or a methyl group;
can be used as perfuming ingredient, for instance to impart odor notes of the musky-earthy and woody, aromatic-fresh character.

For the sake of clarity, by the expression "wherein one dotted line represents a carbon-carbon single or double bond", or the similar, it is meant the normal meaning understood by a person skilled in the art, i.e. that the whole bonding (solid and dotted line) between the carbon atoms connected by said dotted line is a carbon-carbon single or double bond.

According to an embodiment of the invention, said R represents a methyl group.

According to any one of the above embodiments of the invention, when said dotted line represents a carbon-carbon single bond, the two hydrogen atoms bonded to the carbons 4a and 8a are in a relative trans configuration.

According to any one of the above embodiments of the invention, said dotted line represents a carbon-carbon double bond.

As specific examples of the invention's compounds, one may cite, as non-limiting example, 5,5,6,7,8,8-hexamethyl-3,4,5,8-tetrahydro-1(2H)-naphthalenone.

This compound possesses a musky-earthy odor characterized by a pear, woody and aromatic-chamomile-fresh character. The odor of this compound has a surprising musky and fresh combination reminding surprisingly of a mix of the earthy aspect of the well known musk Tonalide® (5,6,7,8-tetrahydro-3,5,5,6,8,8-hexamethyl-2-naphthyl)-1-ethanone; origin: PFW, Holland) and of the fruity/fresh aspect of Helvetolide® ((1S,1'R)-2-[1-(3',3'-dimethyl-1'-cyclohexyl) ethoxy]-2-methylpropyl propanoate; origin: Firmenich SA, Switzerland). When the organoleptic properties of this compound are compared to those of the prior art (6RS,7RS)-5,5,6,7,8,8-hexamethyl-3,4,5,6,7,8-hexahydronaphthalen-1 (2H)-one (described in WO2005/054220), then the invention's compound although having musk-earthy notes distinguishes itself by having a higher impact/strength, strong woody/ambrette note together with a fresh aromatic character of the chamomile type (all absent or almost absent from the prior art compound) and being devoid of significant animal connotation typical of the prior art compound. Furthermore, 5,5,6,7,8,8-hexamethyl-3,4,5,8-tetrahydro-1(2H)-naphthalenone surprisingly possesses odor notes which are as strong/powerful as the prior art analogue (6RS,7RS)-5,5,6,7,8,8-hexamethyl-3,4,5,6,7,8-hexahydronaphthalen-1(2H)-one despite the quite different conformational shape, and this is quite surprising.

As other specific, but non-limiting, examples of the invention's compounds, one may cite the following ones in Table 1:

TABLE 1

Invention's compounds and their odor properties

| Compound structure and name | Odor notes |
| --- | --- |
| 5,5,6,7,8,8-Hexamethyl-3,4,4aα,5,8,8aβ-hexahydro-1(2H)-naphthalenone | Musky, more earthy than the compound below, camphoraceous, almost like eucalyptus, woody/ambrette, not animalic |
| 5,5,6,8,8-Pentamethyl-3,4,5,8-tetrahydro-1(2H)-naphthalenone | Musky, powdery, little bit earthy, with nice aromatic Angelica, chamomile and cardamome aspect, woody/ambrette, not animalic |

According to a particular embodiment of the invention, the compounds of formula (I) are 5,5,6,7,8,8-hexamethyl-3,4,5,8-tetrahydro-1(2H)-naphthalenone, 5,5,6,7,8,8-hexamethyl-3,4,4aα,5,8,8aβ-hexahydro-1(2H)-naphthalenone or 5,5,6,8,8-pentamethyl-3,4,5,8-tetrahydro-1(2H)-naphthalenone.

When the odor of the invention's compounds is compared with that of the prior art, then the invention's compounds distinguish themselves by a clearly stronger woody/ambrette-like note, by having a characteristic aromatic note (absent in the prior art compounds) and by lacking or not possessing a significant, animal notes which are characteristic of some of the prior art compounds. Said differences lend the invention's compounds and the prior art compounds to be each suitable for different uses, i.e. to impart different organoleptic impressions.

The compounds of formula (I), to the best of our knowledge, are also new compounds, and therefore another object of the present invention.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualitat, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added.

Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 45% by weight, or even more, of the compounds of the invention based on the weight of the composition into which they are incorporated. Concentrations lower than these, such as in the order of 0.1% to 20% by weight, can be used when these compounds are incorporated into perfumed articles, percentage being relative to the weight of the article.

The invention's compounds can be prepared according to a method as described in the Examples herein below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

methyl 2,3,3,6,6-pentamethyl-4-oxocyclohex-1-enecarboxylate (2a)

A solution of tBuOK (16.28 g in 70 ml diglyme) and MeI (11.32 ml) were added simultaneously over 1.5 h to a solution of methyl 2,6,6-trimethyl-4-oxocyclohex-2-enecarboxylate (15 g, 72.7 mmol) in diglyme (80 ml) cooled at 0° C. The mixture was stirred at 0° C. for 2 hours and then quenched with HCl 5%. The mixture was extracted with $Et_2O$ and the organic layer was washed with water, saturated $NH_4OH$ solution, water, saturated bicarbonate solution, and brine. The collected organic layers were dried with $MgSO_4$ and the solvents were evaporated. The crude was purified by distillation (125° C., 0.1 mbar) and column chromatography (Silicagel, cyclohexane/EtOAc 98/2) to give (2a). Yield: 27%.

methyl 2,3,3,5,6,6-hexamethyl-4-oxocyclohex-1-enecarboxylate (2b)

A solution of (2a) (1.0 g, 4.38 mmol) in THF (5 ml) was slowly added to a solution of LDA (freshly prepared from 3.13 ml BuLi 1.54M and 0.71 ml of $iPr_2NH$) in THF (5 ml). The solution was stirred at −78° C. for 30 min and then a MeI (0.41 ml) was added. The mixture was stirred at −78° C. for 30 minutes then slowly warmed at room temperature After 1 hour a saturated solution of $NH_4Cl$ was added and the mixture was extracted with pentane. The organic layer was washed with saturated $NH_4Cl$ solution, bicarbonate, and brine. The collected organic layers were dried with $MgSO_4$ and concentrated to dryness. The crude was purified by column chromatography (silicagel, cyclohexane/EtOAc 98/2). Yield 78%.

methyl 4-hydroxy-2,3,3,4,6,6-hexamethylcyclohex-1-enecarboxylate (3a)

A solution of $CeCl_3$ (1.51 equiv.) in THF (75 ml) was stirred at room temp for 1 hour. The suspension was cooled down to −78° C., MeLi (1.50 equiv., 1.46M in $Et_2O$) was slowly added over 10 minutes, followed by the addition of a solution of (2a) (20.31 mmol) in THF (15 ml). After 30 minutes, the mixture was allowed to warm to 0° C. and quenched by adding $NH_4Cl$ and ice. The mixture was extracted with $Et_2O$ and the organic layers were washed with water, saturated bicarbonate solution, and brine. After drying with $MgSO_4$, the solution was concentrated and distilled (125° C., 0.1 mbar). Yield 99%.

methyl 4-hydroxy-2,3,3,4,5,6,6-heptamethylcyclohex-1-enecarboxylate (3a)

As described above for (3a) provided it used (2b) as starting material. Yield 93%.

methyl 2,3,3,4,6,6-hexymethylcyclohexa-1,4-dienecarboxylate (4a)

Compound (3a) (30 mmol) and pTSA (10 w/w %) were dissolved in cyclohexane (90 ml). The mixture was refluxed in a Dean-Stark apparatus for 2 hours. The mixture was cooled at room temperature and a 5% NaOH solution was added. The mixture was extracted with $Et_2O$ and the organic layer was washed with a saturated bicarbonate solution and brine. The collected organic layers were dried with $MgSO_4$ and concentrated. The residue was purified by column chromatography (silicagel, cyclohexane/EtOAc 91/9). Yield: 90%.

methyl 2,3,3,4,5,6,6-heptamethylcyclohexa-1,4-dienecarboxylate (4b)

As described above for (4a) provided it used (3b) as starting material. Yield: 67%.

(E)-(1-(2,2,4,5,5-pentamethyl-6-methylenecyclohex-3-enylidene)allyloxy)trimethylsilane (5a)

A 1.35M solution of nBuLi in hexane (5.85 mmol) was added dropwise to a solution of (4a) (4.50 mmol) in THF (10 ml) cooled at −10° C. When the addition was completed, the cooling bath was removed and the yellow mixture was stirred for 15 min at room temperature. A solution of vinyl magnesium bromide (1M in THF, 5.85 mmol) was added and the mixture was stirred at 35° C. for 30 minutes. The solution was then cooled to −20° C., TMSCl (13.5 mmol) was added within 5 min, and then the solution was stirred at room temp for 50 minutes. After evaporation of the solvents the product was isolated by bulb-to-bulb distillation (130° C., 0.04 mbar) to give a colorless oil. Yield: 73%.

(E)-(1-(2,2,3,4,5,5-hexamethyl-6-methylenecyclohex-3-enylidene)allyloxy)trimethylsilane (5b)

As described above for (5a) provided it used (4b) as starting material. Yield: 75%.

5,5,6,8,8-Pentamethyl-3,4,5,8-tetrahydro-1(2H)-naphthalenone (6a)

A solution containing (5a) (2.5 mmol) in toluene (15 ml) was injected over 1 hour through a 20 cm column packed with quartz tubes heated at 410° C. using argon as carrier. The column was washed with 5 ml of pure toluene and the collected mixture was evaporated to dryness. The concentrate was added to a solution of oxalic acid (1.12 mmol) in THF (10 ml) and water (1 ml) and the mixture was stirred at room temperature for 1 hour then quenched with a saturated bicarbonate solution and extracted with diethylether. The organic layer was washed with water and brine, then dried with $MgSO_4$, and evaporated to dryness. The crude was purified by bulb-to-bulb distillation and column chromatography (Silicagel, Cyclohexane/EtOAc 99/1). Yield: 62%.
$^{13}$C-NMR: 19.0 (q), 23.4 (t), 25.6 (q), 26.9 (t), 28.7 (q), 34.6 (s), 40.3 (t), 40.4 (s), 132.0 (s), 134.0 (d), 136.6 (s), 160.9 (s), 199.9 (s);

5,5,6,7,8,8-Hexamethyl-3,4,5,8-tetrahydro-1(2H)-naphthalenone (6b)

As described above for (6a) provided it used (5b) as starting material. Yield: 47%.
$^{13}$C-NMR: 14.7 (q), 14.9 (q), 23.4 (t), 25.7 (q), 25.8 (q), 27.2 (t), 37.6 (s), 40.6 (s), 40.9 (t), 127.1 (s), 132.7 (s), 136.7 (s), 160.3 (s), 200.0 (s).

5,5,6,7,8,8-Hexamethyl-3,4,4aα,5,8,8aβ-hexahydro-1(2H)-naphthalenone

A mixture of (6b) (1.97 g, 6.03 mmol) and Pd/C (10%, 200 mg) and EtOH (20 ml) was stirred in a pressure reactor under $H_2$ (80 bar) at 75° C. for 7 hours. The mixture was filtered and the filtrate concentrated. The crude was purified by column chromatography (Silicagel, pentane/$Et_2O$ 99:1). Yield: 46%.
$^{13}$C-NMR: 14.6 (q), 15.1 (q), 20.6 (q), 21.5 (q), 22.2 (t), 24.4 (t), 26.0 (q), 26.0 (q), 38.4 (s), 38.6 (s), 41.1 (t), 43.7 (d), 57.1 (d), 132.6 (s), 133.4 (s), 215.0 (s).

Example 2

Preparation of a Perfuming Composition

A perfuming composition for shower gel was prepared by admixing the following ingredients:

| Parts by weight | Ingredient |
|---|---|
| 150 | Benzyl acetate |
| 20 | Geranyl acetate |
| 10 | Aldehyde C 11 lic |
| 400 | Hexylcinnamic Aldehyde |
| 20 | Ambrox ®[1] |
| 20 | Gamma undecalactone |
| 20 | Methyl benzoate |
| 150 | Citronellol |
| 100 | Coumarine |
| 100 | Cyclosal |
| 10 | 10%* Damascenone |
| 30 | Estragole |
| 1200 | Florol ®[2] |
| 400 | Hedione ®[3] HC |
| 100 | 1,3-Benzodioxole-5-carbaldehyde |
| 250 | ISO E ®[4] Super |
| 250 | Alpha iso-methyl ionone |
| 100 | Jasmin essential oil |
| 350 | Linalool |
| 50 | Crystal moss |
| 800 | Hedione ®[5] |
| 350 | Phenethylol |
| 20 | Polysantol ®[6] |
| 100 | Vanilline |
| 100 | Violette essential oil |
| 200 | Bergamote essential oil |
| 200 | Ylang essential oil |
| 5500 | |

*in dipropyleneglycol
[1] (−)-(8R)-8,12-epoxy-13,14,15,16-tetranorlabdane; origin: Firmenich SA, Geneva, Switzerland
[2] tetrahydro-2-isobutyl-4-methyl-4(2H)-pyranol; origin: Firmenich SA, Geneva, Switzerland
[3] methyl cis-dihydrojasmonate; origin: Firmenich SA, Geneva, Switzerland
[4] 1-(octahydro-2,3,8,8-tetramethyl-2-naphtalenyl)-1-ethanone; origin: International Flavors & Fragrances, USA
[5] methyl dihydrojasmonate; origin: Firmenich SA, Geneva, Switzerland
[6] 3,3-dimethyl-5-(2,2,3-trimethyl-3-cyclopenten-1-yl)-4-penten-2-ol; origin: Firmenich SA, Geneva, Switzerland The addition of 4500 parts by weight of 5,5,6,7,8,8-hexamethyl-3,4,5,8-tetrahydro-1(2H)-naphthalenone to the above-described composition imparted to the latter a strong musky odor and reinforced the clean fresh-aldehydic topnote. It also pushed the woody aspect of the fragrance.

When instead of the invention's compound was used the same amount of the prior art (6RS,7RS)-5,5,6,7,8,8-hexamethyl-3,4,5,6,7,8-hexahydronaphthalen-1(2H)-one, the addition gave a lower degree of muskyness, which was also less clean and more earthy and animalic, and pushed the powderyness side of the composition.

Example 3

Preparation of a Perfuming Composition

A perfuming composition for eau de toilette for men was prepared by admixing the following ingredients:

| Parts by weight | Ingredient |
|---|---|
| 100 | Benzyl acetate |
| 100 | Badiane essential oil |
| 1500 | Bergamote essential oil |
| 150 | Cinnamon oil |
| 50 | Cardamome |
| 30 | Ciste essential oil |
| 600 | Coumarine |
| 100 | Ethylvanilline |
| 400 | Eugenol |
| 50 | Ginger oil |
| 400 | Hedione ®[1) HC |
| 10 | Isobutylquinoleine |
| 700 | Lavender essential oil |
| 1000 | Linalool |
| 400 | Lyral ®[2) |
| 400 | Mandarine essential oil |
| 100 | Mint essential oil |
| 20 | Crystal moss |
| 700 | Nirvanol ®[3) |
| 20 | Patchouli oil |
| 300 | Santal essential oil |
| 200 | Sclary sage |
| 500 | Ylang |
| 80 | Civette |
| 40 | Pine essential oil |
| 50 | White thyme |
| 8000 | |

*in dipropyleneglycol
[1)]methyl cis-dihydrojasmonate; origin: Firmenich SA, Geneva, Switzerland
[2)]4/3-(4-hydroxy-4-methylpentyl)-3-cyclohexene-1-carbaldehyde; origin: International Flavors & Fragrances, USA
[3)]3,3-dimethyl-5-(2,2,3-trimethyl-3-cyclopenten-1-yl)-4-penten-2-ol; origin: Firmenich SA, Geneva, Switzerland The addition of 2000 parts by weight of 5,5,6,7,8,8-hexamethyl-3,4,5,8-tetrahydro-1(2H)-naphthalenone to the above-described composition imparted to the latter a clean (not animal) musky-ambrette twist, boosted the aromatic notes increasing the freshness of the original composition and added a hint of fruitiness.

When instead of the invention's compound was used the same amount of the prior art (6RS,7RS)-5,5,6,7,8,8-hexamethyl-3,4,5,6,7,8-hexahydronaphthalen-1(2H)-one, the addition did not bring any freshness, but instead imparted a powdery and animal side of the original composition.

The fragrance obtained by the addition of the invention's compound was significantly different in character compared with the one obtained by the addition of the prior art compound.

What is claimed is:

1. A compound having an odor character that includes a woody/ambrette-like note having a characteristic aromatic note and lacking or not possessing any significant, animal notes, the compound being of formula

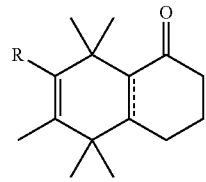

(I)

wherein the dotted line represents a carbon-carbon single or double bond and R represents a hydrogen atom or a methyl group.

2. A compound according to claim 1, wherein R represents a methyl group.

3. A compound according to claim 1 or 2, wherein said dotted line represents a carbon-carbon double bond.

4. A compound according to claim 1, specifically as 5,5,6,7,8,8-hexamethyl-3,4,5,8-tetrahydro-1(2H)-naphthalenone 5,5,6,7,8,8-hexamethyl-3,4,4aα,5,8,8aβ-hexahydro-1(2H)-naphthalenone or 5,5,6,8,8-pentamethyl-3,4,5,8-tetrahydro-1(2H)-naphthalenone.

5. A method to confer, enhance, improve or modify the odor properties of a perfuming composition or of a perfumed article, which method comprises adding to said composition or article an effective amount of at least a compound of formula (I)

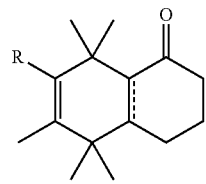

(I)

wherein the dotted line represents a carbon-carbon single or double bond and R represents a hydrogen atom or a methyl group, wherein the compound has an odor character that includes a woody/ambrette-like note having a characteristic aromatic note and lacking or not possessing any significant, animal notes.

6. The method of claim 5, wherein R represents a methyl group.

7. The method of claim 5, wherein said dotted line represents a carbon-carbon double bond.

8. The method of claim 5, wherein the compound is 5,5,6,7,8,8-hexamethyl-3,4,5,8-tetrahydro-1(2H)-naphthalenone 5,5,6,7,8,8-hexamethyl-3,4,4aα,5,8,8aβ-hexahydro-1 (2H)-naphthalenone or 5,5,6,8,8-pentamethyl-3,4,5,8-tetrahydro-1(2H)-naphthalenone.

9. A perfuming composition comprising
i) at least one compound of formula (I)

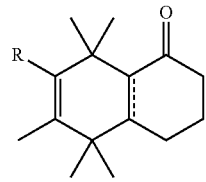

(I)

wherein the dotted line represents a carbon-carbon single or double bond and R represents a hydrogen atom or a methyl group;

ii) at least one ingredient selected from the group consisting of a perfumery carrier and a perfumery base; and iii) optionally at least one perfumery adjuvant.

10. The perfuming composition of claim 9, wherein R represents a methyl group.

11. The perfuming composition of claim 9, wherein said dotted line represents a carbon-carbon double bond.

12. The perfuming of claim 9, wherein the compound is 5,5,6,7,8,8-hexamethyl-3,4,5,8-tetrahydro-1(2H)-naphthalenone, 5,5,6,7,8,8-hexamethyl-3,4,4a$\alpha$,5,8,8a$\beta$-hexahydro-1(2H)-naphthalenone or 5,5,6,8,8-pentamethyl-3,4,5,8-tetrahydro-1(2H)-naphthalenone.

* * * * *